US00PP37427P2

(12) United States Plant Patent
Clark

(10) Patent No.: US PP37,427 P2
(45) Date of Patent: May 12, 2026

(54) ***LAVANDULA* PLANT NAMED 'ARKEZIE'**

(50) Latin Name: *Lavandula augustifolia*
Varietal Denomination: ARKEZIE

(71) Applicant: Richard Clark, Dereham (GB)

(72) Inventor: Richard Clark, Dereham (GB)

( * ) Notice: Subject to any disclaimer, the term of this patent is extended or adjusted under 35 U.S.C. 154(b) by 0 days.

(21) Appl. No.: 19/344,456

(22) Filed: Sep. 29, 2025

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./445
See application file for complete search history.

*Primary Examiner* — Susan Mccormick Ewoldt
(74) *Attorney, Agent, or Firm* — Penny J. Aguirre

(57) ABSTRACT

A new cultivar of *Lavandula* plant named 'ARKEZIE' that is characterized by its 5 compact and dwarf plant habit, its flower colors that change from white to blue-purple-pink, and its cold hardiness to 5° fahrenheit.

3 Drawing Sheets

Botanical classification: *Lavandula angustifolia.*
Variety denomination: 'ARKEZIE'.

BACKGROUND OF THE INVENTION

The present invention relates to a new and distinct cultivar of *Lavandula angustifolia* and will be referred to hereafter by its cultivar name, 'ARKEZIE'. 'ARKEZIE' is a new variety of English lavender plant suitable for landscape and container use.

The new cultivar was discovered as a chance seedling by the Inventor in 2019 in the Inventor's garden in North Elmham, Norfolk, England. The parents are unknown, however the one parent plant is believed to be *Lavandula* 'Ashdown Forest' (not patented) based on the characteristics of the new cultivar and its proximity to the claimed plant in the garden of the discovery.

Asexual propagation of the new cultivar was first accomplished by the inventor by softwood stem cuttings in 2019 in in North Elmham, Norfolk, England. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'ARKEZIE' as a unique cultivar of *Lavandula.*

1. 'ARKEZIE' exhibits a compact and dwarf plant habit.
2. 'ARKEZIE' exhibits flower colors that change from white to blue-purple-pink.
3. 'ARKEZIE' exhibits cold hardiness to 5° fahrenheit.

A probable parent plant of 'ARKEZIE' differs from 'ARKEZIE' in having flowers that are pale lavender in color, a larger plant size, longer flower stems, less branching, and a less compact plant habit. 'ARKEZIE' can also be compared to the *Lavandula angustifolia* cultivars 'Nana Alba' (not patented) and 'Kerbeepink' (U.S. Plant Pat. No. 32,795). 'Nana Alba' is similar to 'ARKEZIE' in having a mound forming plant habit and light colored flowers. 'Nana Alba' differs from 'ARKEZIE' in having white color flowers, smaller flowers, and less branching. 'Kerbeepink' is similar to 'ARKEZIE' in having a compact and mounded plant habit. 'Kerbeepink' differs from 'ARKEZIE' in having flowers that are light pink in color, less branching, and longer and less compact foliage.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Genesis Plant Marketing (the breeders representative), Stewarts Garden Centre, Sturmer Nurseries Garden Centre (facebook), and Coolings.

BRIEF DESCRIPTION OF THE DRAWINGS

The accompanying color photographs illustrate the overall appearance of the distinct characteristics of an 18-month-old plant of the new cultivar as grown outdoors in a 19-cm container in Boskoop, The Netherlands.

The photograph in FIG. 1 illustrates a side view of 'ARKEZIE' in bloom.

Figure 1:
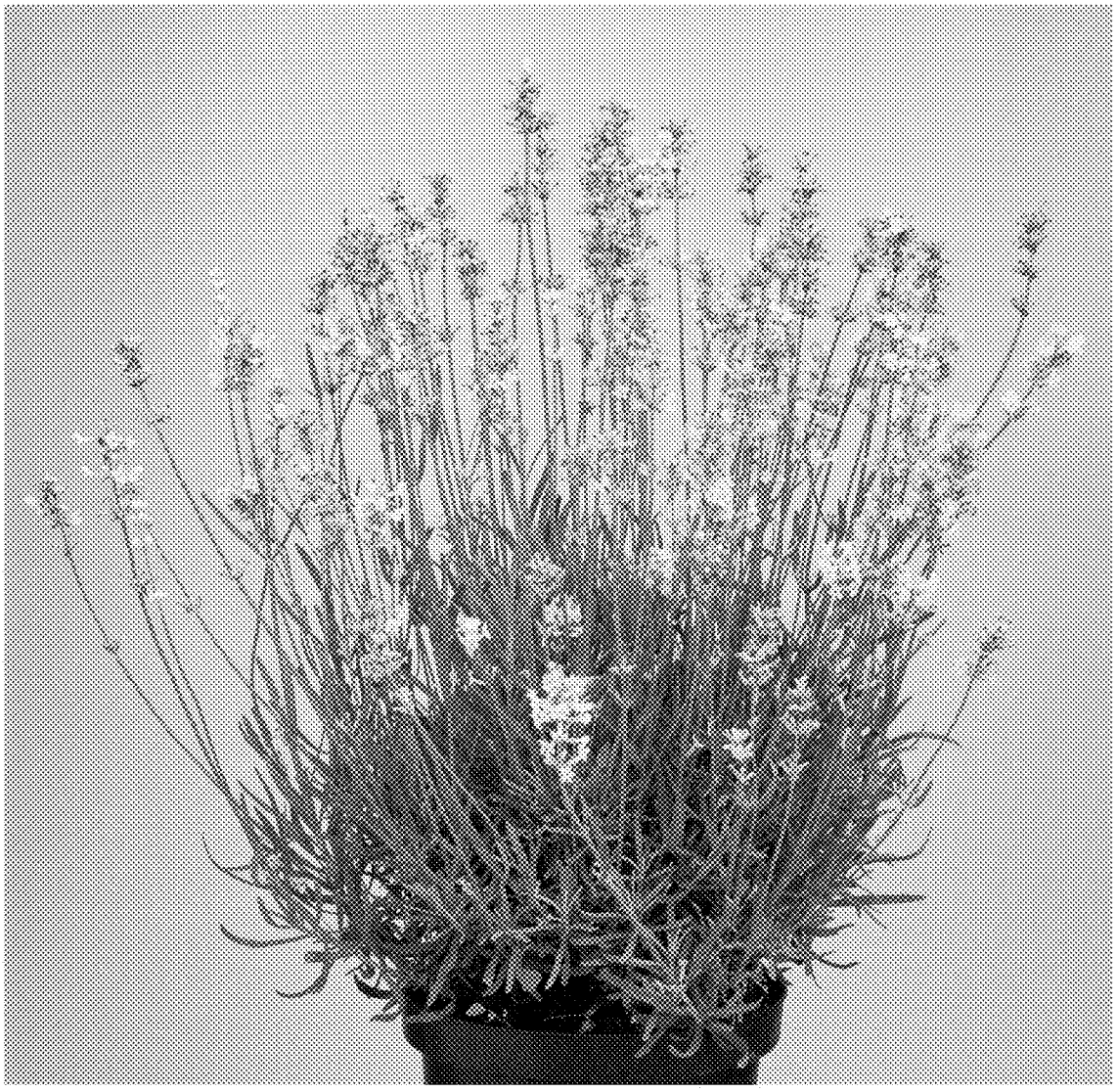
Figure 2:
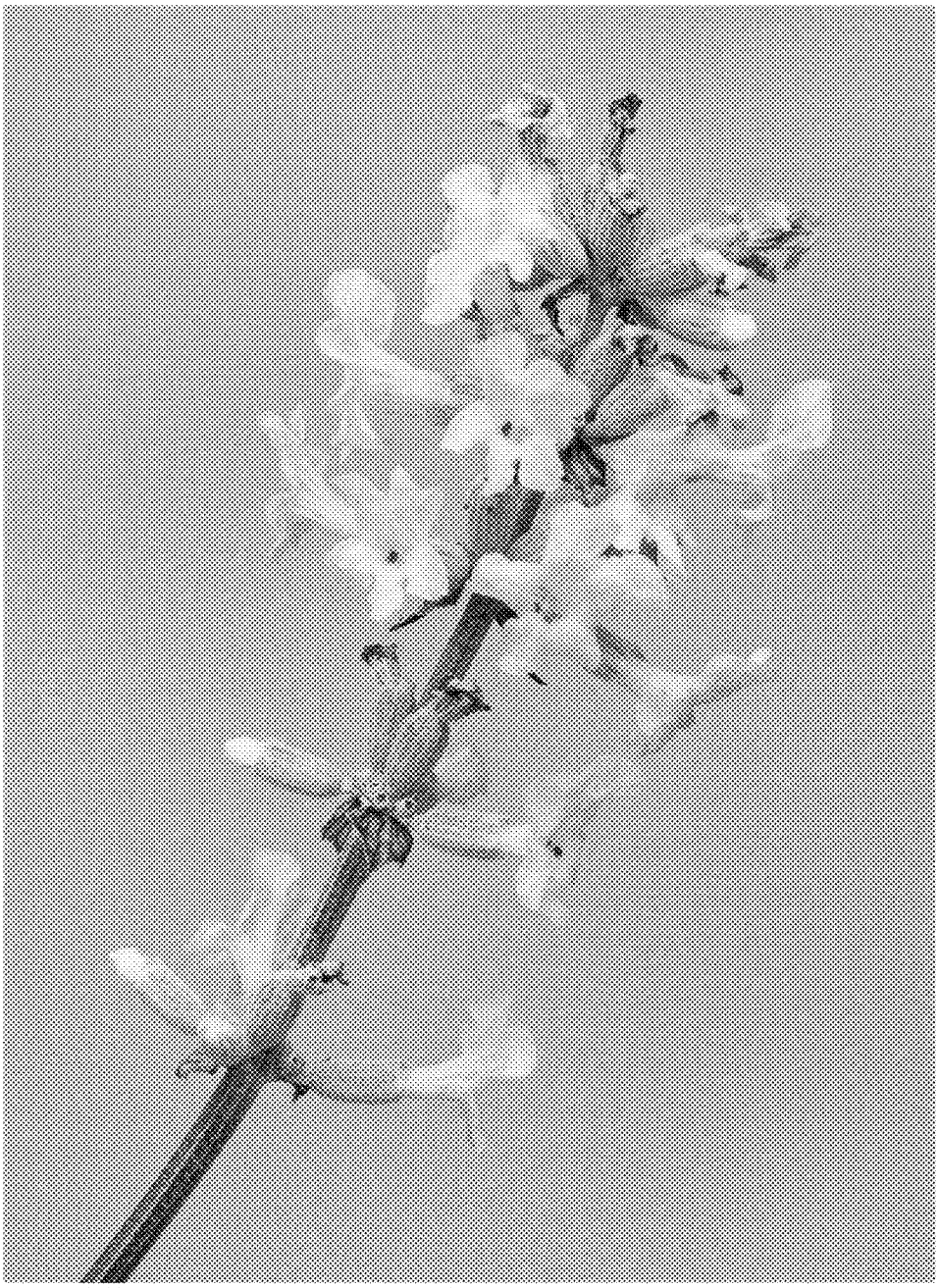

The photograph in FIG. 2. provides a close up view of an inflorescence of 'ARKEZIE'.

Figure 3:
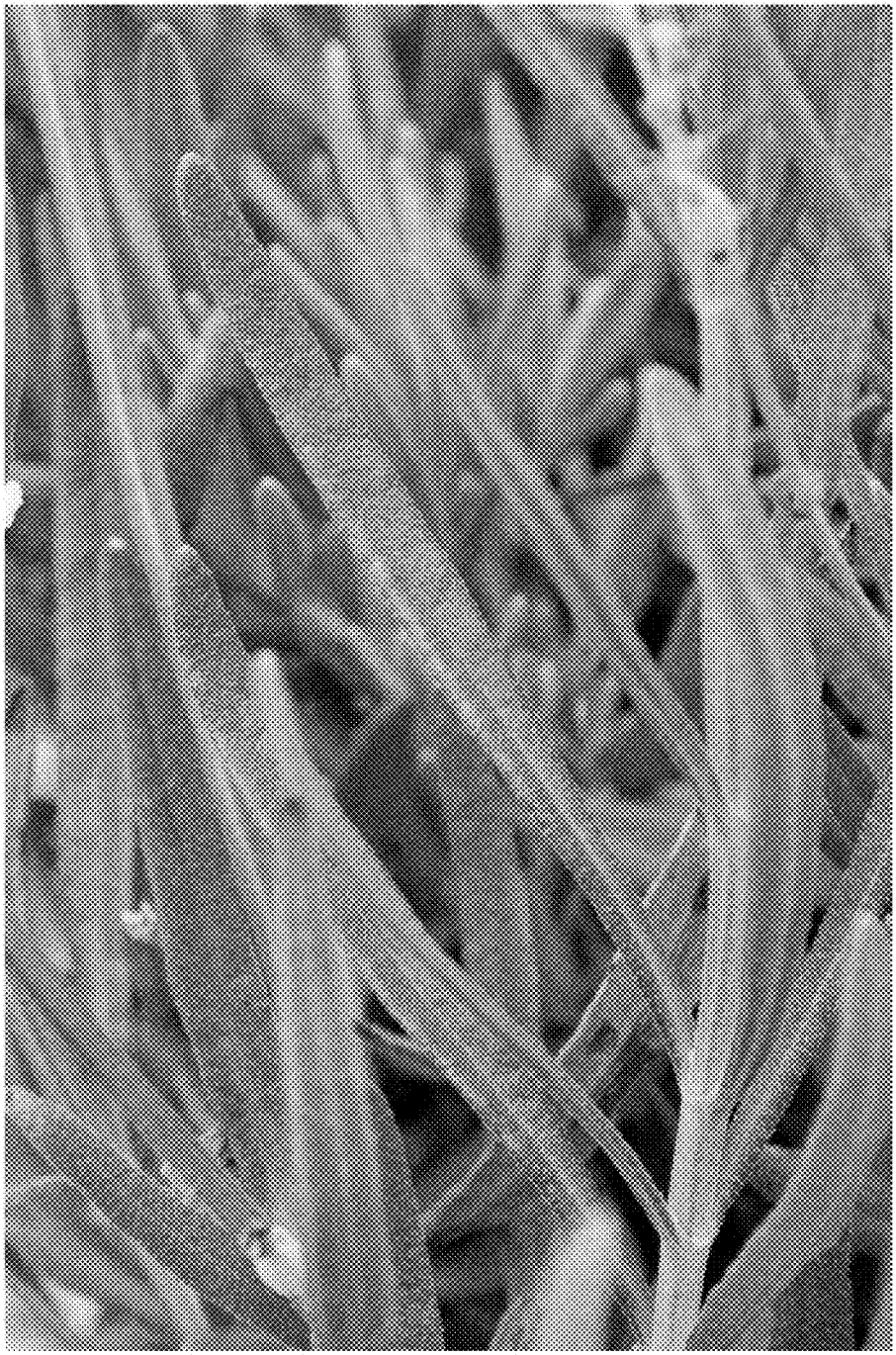

The photograph in FIG. 3. provides a close up view of the foliage of 'ARKEZIE'.

The colors in the photographs are as close as possible with the digital photography techniques utilized and the color values cited in the detailed botanical description accurately describe the colors of the new *Lavandula.*

DETAILED BOTANICAL DESCRIPTION

The following is a detailed description of 18-month-old plants of the new cultivar as grown outdoors in 19-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Late spring to summer in The United Kingdom.

*Plant type*.—Perennial, subshrub.

*Plant habit*.—Compound, mounded foliage with flowering stems held above foliage, bushy.

*Height and spread*.—Reaches 31.2 cm in height to the top of the foliage plane, 45.5 cm in height to the top of the floral plane, and 38.5 cm in spread as an 18-month-old plant grown in a container.

*Hardiness*.—At least in U.S.D.A. Zones 6 to 10.

*Diseases and pests*.—No susceptibility or resistant to pests or diseases has been observed.

*Root description*.—Thin and fibrous.

*Root development*.—Time required for root initiation; 4 to 6 weeks, time required to produce a young plant from a rooted cutting; 24 weeks to produce a 9-cm container.

*Propagation*.—Softwood stem cuttings.

*Growth*.—Moderate to vigorous.

Stem description:

*Stem shape*.—Quadrangular.

*Stem color*.—Young; 145B, mature; 144A, old bark; 199B.

*Stem surface*.—Moderately glandular tomentose with hairs <0.1 mm in length and too fine to measure color, matte.

*Stem size*.—Average of 11.4 cm in length and 2 mm in width.

*Stem strength*.—Moderately strong.

*Stem aspect*.—Main branches held at an average angle of 30° to vertical, lateral branches held at an average angle of 35° to main branches.

*Branching*.—Main; 14, lateral; 10 per main branch.

*Internode length*.—2.9 cm.

Foliage description:

*Leaf shape*.—Narrowly oblong.

*Leaf division*.—Simple.

*Leaf base*.—Cuneate.

*Leaf apex*.—Acute.

*Leaf venation*.—Pinnate, upper surface; 145B, lower surface; 144A.

*Leaf margins*.—Entire, slightly revolute, unlobed.

*Leaf arrangement*.—Opposite.

*Leaf attachment*.—Sessile.

*Leaf number*.—Average of 12 lateral stem.

*Leaf surface*.—Both surfaces are densely glandular pubescent, 0.1 mm in length, matches leaf surfaces, matte.

*Leaf size*.—Average of 4.7 cm in length and 5 mm in width.

*Leaf color*.—Young upper surface; 138B, young lower surface; 143C, mature upper surface; NN137B, mature lower surface; 146B.

*Leaf fragrance*.—Strongly fragrant, typical *Lavandula* scent.

Inflorescence description:

*Inflorescence type*.—Terminal spike, individual flowers in verticillasters.

*Inflorescence number*.—1 Spike per flowering stem.

*Inflorescence fragrance*.—None.

*Lastingness of inflorescence*.—Average of 4 weeks with open flowers, flowers last an average of 2 days.

*Inflorescence size*.—7.2 cm in height (excluding peduncle) and 2.1 cm in width.

*Flower number*.—Average of 70 per inflorescence, average of 8,400 flowers and buds per plant.

*Flower buds*.—Average of 6 mm in length, 1.75 mm in diameter, oblong in shape, surface is densely pubescent, matte, color: 138D, veins 144C, immature upper sepal tips 161B, top of immature petals 69D.

*Flowers*.—Outward aspect, self-cleaning, salviform in shape, petals fused into one upper lip (split into 2 identical petal lobes), and one lower lip (split into three identical petal lobes), 8 mm in height, 7 mm in diameter, 1 cm in depth, throat 1.5 mm in diameter, tube 6.5 mm in length and 1.5 mm in diameter.

*Petals*.—Rotate, 5 petals fused into a salverform arrangement, spathulate shape, obtuse apex, lower portion fused into a tube, upper petals; 4 mm in length, 2 mm in width, lower petals 3 mm in length and 1.5 mm in width, margins entire and slightly reflexed, low to medium undulation, all surfaces smooth and moderately velvety, color: upper and lower surface when opening; 69D, upper and lower surface when fully open; 75C, fading to 76A, throat; 76C, tube; upper 75D, middle 75B, base N155B.

*Calyx*.—Rotate, tubular, average of 5 mm in length and 2 mm in diameter.

*Sepals*.—5, 1 whorl, 5 mm in length, 0.5 mm in width, 95% of the sepals fused into a tube, linear in shape and fused into a tubular shape, acute apex with upper sepal obtuse, base fused, 5% free, margins entire, both surfaces densely pubescent, upper surface slightly glossy, lower surface matte, color: when opening and fully open upper surface; 145C, veins 146C, tip 195B, when opening and fully open lower surface; 145B, 146C, tip 195A and 195B.

*Peduncles*.—Strong, average of 19.3 cm in length and 0.5 mm in diameter, 0° angle to lateral branch, surface is moderately covered with grandular tomentose hairs <0.1 mm in length, matte, 138A in color.

*Pedicels*.—Strong, average of 1 mm in length and 2 mm in diameter, 50° angle to peduncle, surface is moderately covered with grandular tomentose hairs <0.1 mm in length, matte, 145B in color.

*Flower bracts*.—A single floral bract is placed at the base of each verticillaster, rhomboidal in shape, average of 4 mm in length and width, margins on upper half finely dentate, lower half entire, apex aristate, base broad acuminate, upper surface glossy, lower surface matte, color: both surfaces transparent 145D in color, veins 145B, lower surface and margins moderately covered with glandular tomentose pubescence.

Reproductive organs:

*Pistils*.—1, pistil; 5 mm in length, stigma; narrow club-shaped, 177D in color, style; 4 mm in length, N155A in color, ovary; 147A in color.

*Stamens*.—4, anthers; dorsifixed, short oblong in shape, average of 0.5 mm in length, 203A in color, filament; 1 mm in length, 69D in color, pollen; low in quantity, 155D in color.

It is claimed:

1. A new and distinct cultivar of *Lavandula* plant named 'ARKEZIE' as herein illustrated and described.

* * * * *